United States Patent
Sivard et al.

[11] Patent Number: 5,458,115
[45] Date of Patent: Oct. 17, 1995

[54] DETECTOR FOR SENSING EVENTS IN LIVING TISSUE

[75] Inventors: Ake Sivard, Solna; Kurt Hoegnelid, Voesterhuninge, both of Sweden

[73] Assignee: Siemens Elema AB, Solna, Sweden

[21] Appl. No.: 152,126

[22] Filed: Nov. 16, 1993

[30] Foreign Application Priority Data

Dec. 3, 1992 [SE] Sweden .................... 9203642

[51] Int. Cl.⁶ .................................. A61B 5/0472
[52] U.S. Cl. ...................................... 128/708
[58] Field of Search ............ 128/906, 708, 128/901

[56] References Cited

U.S. PATENT DOCUMENTS

| | | | |
|---|---|---|---|
| 3,174,478 | 3/1965 | Kahn | 128/706 |
| 3,878,833 | 4/1975 | Arneson et al. | 128/708 |
| 4,041,953 | 8/1977 | Anderson et al. | |
| 4,708,144 | 11/1987 | Hamilton et al. | |
| 4,766,902 | 8/1988 | Schroeppel | |
| 5,050,599 | 9/1991 | Hoegnelid | |
| 5,103,819 | 4/1992 | Baker et al. | |

FOREIGN PATENT DOCUMENTS 0321764 6/1989 European Pat. Off. .

*Primary Examiner*—William E. Kamm
*Attorney, Agent, or Firm*—Hill, Steadman & Simpson

[57] ABSTRACT

A detector for sensing events in living tissue, such as electrical events in a heart, contains a microprocessor functioning as comparator which compares an input signal corresponding to electrical signals from the living tissue with a defined signal detection level, and an event is deemed to have occurred if the input signal exceeds the defined detection level. More reliable detection of events in the presence of noise is achieved by also providing an integrator which generates the input signal to the comparator by integrating electrical signals obtained from the tissue, the comparator then comparing the integrated signal with a detection level selected for use with the integrated signal.

14 Claims, 2 Drawing Sheets

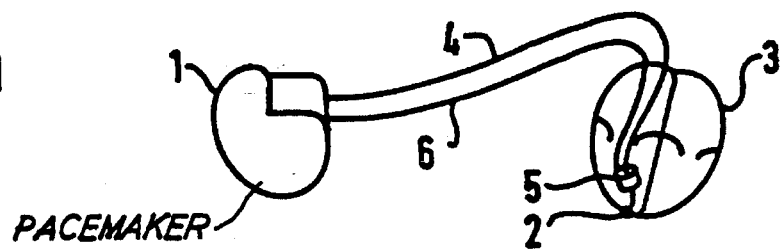
FIG 1
PACEMAKER
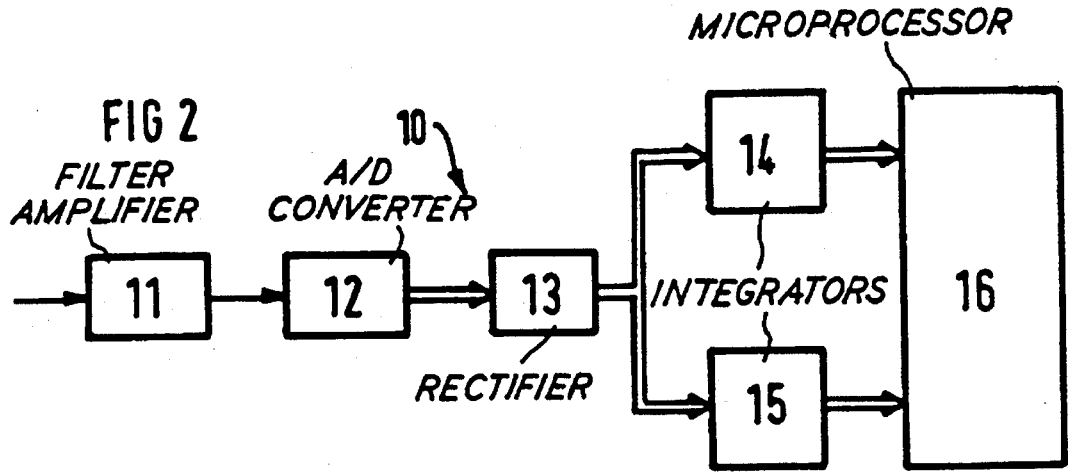
FIG 2 — FILTER AMPLIFIER 11, A/D CONVERTER 12, RECTIFIER 13, INTEGRATORS 14, 15, MICROPROCESSOR 16
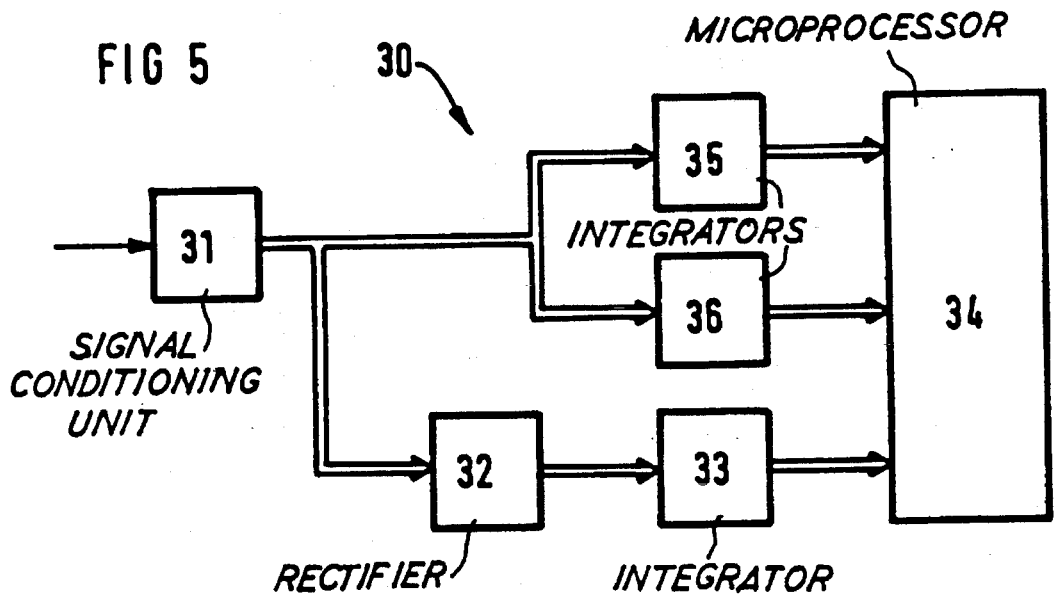
FIG 5 — SIGNAL CONDITIONING UNIT 31, INTEGRATORS 35, 36, RECTIFIER 32, INTEGRATOR 33, MICROPROCESSOR 34

DETECTOR FOR SENSING EVENTS IN LIVING TISSUE

BACKGROUND OF THE INVENTION

1. Field of the Invention

The present invention is directed to a detector for sensing events in living tissue of the type having a comparator which compares an input signal corresponding to electrical signals from the tissue with a defined level of signal detection, an event being deemed to have occurred if the input signal exceeds the defined level of detection.

2. Description of the Prior Art

A pacemaker is disclosed in U.S. Pat. No. 4,041,953 which emits stimulation pulses to a heart when the heart does not beat spontaneously (naturally). In order to detect spontaneous events, the electrical signals of the heart are sensed, amplified and sent to a level detector which determines whether the amplitude of the cardiac signal exceeds a detection level. A spontaneous heartbeat is deemed to have occurred if the amplitude exceeds the detection level, and emission of a stimulation pulse is inhibited.

In U.S. Pat. No. 4,708,144 a pacemaker is disclosed which, in a similar manner, senses electrical signals from the heart and interprets the signal as representative of spontaneous cardiac activity if the amplitude of the signal exceeds a specified detection level. The detection level is automatically adjusted by measurement of the peak value of the R-wave in the cardiac signal, and a long-term average is calculated. The detection level is then set according to the average value determined in this manner.

A problem with amplitude detectors of this type is that the measurement signal often contains electrical noise from the surroundings. The physician must program the detector in the pacemaker disclosed in U.S. Pat. No. 4,041,953 with a specified detection level. This procedure is normally performed at a clinic in quiet, noise-free conditions. After the patient leaves the clinic, however, the detector may interpret noise from electrically noisier surroundings as spontaneous heart beats. The pacemaker would then be inhibited under circumstances when a stimulation pulse was actually necessary.

This problem is partially addressed by incorporating automatic setting of the detection level, as in the pacemaker disclosed in U.S. Pat. No. 4,708,144. The relationship between the detection level and the average value for peak values of R-waves results in some adaptation of the signal, picked up by the electrode, which contains the noise. The averaging of peak values takes place over a relatively long period of time, i.e., over at least several minutes. As a result, adaptation requires a few minutes after any change from a noise-free environment to a noisy environment. During this adaptation time, the noise may be interpreted as spontaneous heartbeats, or some spontaneous heartbeats could be missed. In addition, the noise must have a frequency different from the frequency of the spontaneous heartbeat rate if the level of detection is to be able to effectively compensate for that noise. This means that measurement of the R-wave will not help if the noise has the same frequency as the heart rate.

Another problem, which neither of the above-known two detectors addresses, is that of so-called far-field signals. Far-field signal is a signal which takes place in tissue which is relatively remote from the tissue being sensed, but which nonetheless is detected at the sensing site, and is thus interpreted as arising at the sensing site. For example, an event (spontaneous or stimulated) in the ventricle can be sensed in the atrium with an amplitude equal to the amplitude of a true event in the atrium. An ability to distinguish between signals with different sites of origins would thus be useful in many situations.

SUMMARY OF THE INVENTION

It is an object of the present invention to provide a detector for sensing events in living tissue which avoids the above problems and which is capable of reliably distinguishing events in living tissue from noise.

A further object of the present invention is to provide such a detector which automatically adapts the level of detection dependent on the level of noise.

A further object of the present invention is to provide such a detector which automatically adapts the expiration of a refractory period, in which the detector does not sense any events, to the prevailing noise and signal levels.

The first object is achieved in accordance with the principles of the present invention in a detector for sensing events in living tissue having an integrator which generates the input signal supplied to a microprocessor, functioning as the comparator, by integrating the incoming electrical signals from the tissue over a predetermined integration interval.

The integration, which preferably lasts for an integration interval of 5 to 50 ms, provides the area beneath the electrical signals obtained from the tissue, instead of the amplitude of those signals, as a decision parameter for the comparison. For brief periods of time, corresponding to 5 to 10 cardiac cycles, a spontaneous event generates, in principle, the same area, event after event. Noise contributes to the area beneath the curve to an extent which relatively constant over two consecutive integration intervals. The effect of noise on the signal can thus be easily identified as the events taken into account arise over longer intervals, compared to the integration interval. A detector of this type can be used to advantage with an amplitude detector (the function of which can also be accomplished in the microprocessor), to increase the reliability of decisions made by the amplitude detector as to whether an event has occurred.

A refinement of the detector is achieved in a further embodiment of the invention wherein the microprocessor functioning as the comparator compares the input signal to a threshold value which is higher than the detection level, and an event is deemed to have occurred if the input signal exceeds the detection level without exceeding the threshold level during a defined first interval.

Since an interval is predetermined for the integrated area in which the input signal must be located for a given period of time in order for an event to be "approved," this means that severe, transient noise can easily be distinguished from true events.

Preferably, the microprocessor of the detector also function as an averager which determines, from a set number of events, the average value of the peak values of the input signal during a second predetermined interval after the input signal exceeds the detection level. The microprocessor sets the detection level and/or the threshold level on the basis of this average value.

In principle, the peak value arising after the input signal exceeds the detection level corresponds to the maximum area in an event. This makes the determination made in accordance with the principles of the present invention more independent of the noise frequency than the determination which occurs in the above-described prior art pacemaker disclosed in U.S. Pat. No. 4,708,144. In accordance with the principles of the present invention, the microprocessor function as the averager forms a normal value for the integral of the event, and sets the detection and threshold levels on the basis thereof.

The detector can be devised so the microprocessor sets the detection level at a first predetermined fraction of the average value and sets the threshold level at the average value plus a second predetermined fraction of the average value.

In a further embodiment of the detector of the invention, the detector includes a second integrator, which integrates the electrical signal over a longer integration interval than the first-described integrator, preferably 5 to 20 times longer. This results in the generation of a compensatory signal corresponding to prevailing noise superimposed on the electrical signals. The compensatory signal is supplied to the control device in order to compensate the input signal, or the detection level, for prevailing noise.

Because events (e.g., the heart's QRS wave) are chronologically very brief compared to inter-event periods, and noise can be regarded as relatively constant over brief periods of time, integration over 50 to 1000 ms produces a value for the prevailing level of noise. When the period of integration is in the lower part of the interval, the lowest value for the last second (s) should be used as the value for the prevailing level of noise. This value is employed as the compensatory signal for either direct compensation of the input signal or for controlling the detection level.

Preferably, the microprocessor sets the detection level and/or the threshold value dependent on the average value and the compensatory signal.

The detector preferably includes a rectifier which rectifies the incoming electrical signals before they are integrated. Because the electrical signals generated by an event can have positive or negative polarity, the signals are rectified to prevent the two polarities from canceling each other in the calculation of the integral.

Alternatively, in a further embodiment of the invention, the first integrator can integrate electrical signals with a first polarity, and the detector can be provided with an additional integrator which integrates electrical signals with a second polarity, opposite to the first polarity.

In this manner, the detector can easily distinguish between signals with only one polarity (positive or negative) and signals with two polarities (positive and negative) on the basis of the output signals from the first integrator and the additional integrator. Signals which, for example, originate in the atrium of a heart are detected as biphasic in the atrium and monophasic in the ventricle, and vice-versa. This permits the detector to easily determine whether a signal originates in the atrium or in the ventricle. Changing the sign of the output signal from one of the integrators and then adding the two output signals produces the same result as if the signal had been rectified and integrated in a single integrator.

In a further embodiment of the invention, the integrated electrical signals are emitted by the integrator or integrators at intervals shorter than the integration interval.

This results in a floating integral value in which, for example, an integral value for the last 20 ms can be emitted every fifth ms. This increases the operational speed of the detector, and compensates for the delay caused by integration. To prevent double detection during an event, in a further embodiment of the invention the microprocessor inhibits detector from sensing events during a defined refractory period after each sensed event. This normally takes place in a pacemaker even after an emitted stimulation pulse.

In this embodiment it is preferable to set the end of the refractory period at a third defined interval after the input signal drops below the detection level following a detected event.

Alternatively, the refractory period can be set to expire when the input signal falls below the compensatory signal.

DESCRIPTION OF THE DRAWINGS

FIG. 1 is a schematic illustration showing a pacemaker, in which a detector constructed and operating in accordance with the principles of the present invention can be incorporated for sensing spontaneous heartbeats.

FIG. 2 is a schematic block diagram of a first embodiment of a detector constructed in accordance with the principles of the present invention.

FIG. 5 is a schematic block diagram of a second embodiment of a detector constructed in accordance with the principles of the present invention.

DESCRIPTION OF THE PREFERRED EMBODIMENTS

Figure 3:
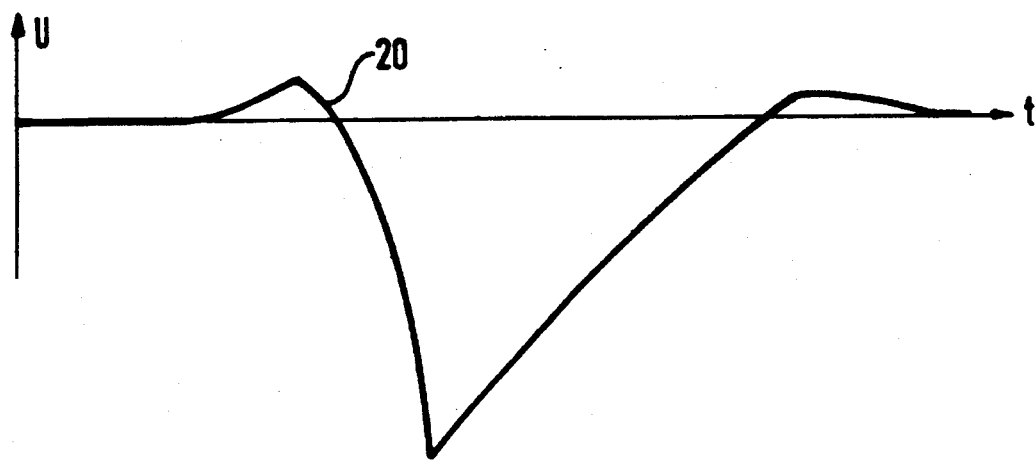
FIG. 3 is a diagram showing the general shape of an electrical signal corresponding to a spontaneous heartbeat.

A pacemaker 1 is shown in FIG. 1 connected to a heart 3 via a tip electrode 2 in the ventricle of the heart 3 carried by a first electrode line 4, and via a ring electrode 5 carried by a second electrode line 6. The pacemaker 1 generates and emits stimulation pulses to the heart 3 in the absence of spontaneous cardiac activity (demand pacemaker).

In order to detect spontaneous heart activity, the pacemaker 1 contains a detector 10 as shown in FIG. 2. The detector 10 contains a filter amplifier 11 which amplifies and filters incoming electrical signals obtained from the heart 3. The filtered and amplified signals from the heart 3 at the output of the filter amplifier 11 are then digitized in an A/D converter 12, and are supplied to a rectifier 13. The rectified signal is then supplied to a first integrator 14 which, after the signal has been digitized, functions as an adder which adds the digitized signal over a first integration interval, for example, 20 ms. The rectified signal is also supplied to a second integrator 15 which integrates the rectified signal over a longer integration period, for example 200 ms. The integrated signal which is the output of the first integrator 14 is supplied to a microprocessor 16 at intervals of 5 ms, and integrated signal which is the output of the second integrator 15 is supplied to the microprocessor 16 at intervals of 100 ms. In the microprocessor 16, the integrated signals are used for identifying spontaneous cardiac events. The microprocessor 16 performs software-conducted comparisons of the signal from the first integrator 14 and a detection level which is set by the two integrated signals. The microprocessor 16 also performs averaging on the incoming signals in a known manner.

It will understood that the detector 10 can alternatively be constructed using analog components.

FIG. 3 shows the general appearance of a heart signal 20 when measured at the tip electrode 2 of the pacemaker 1. The large negative pulse is characteristic of the cardiac signal, and is known as the R-wave.

Figure 4:
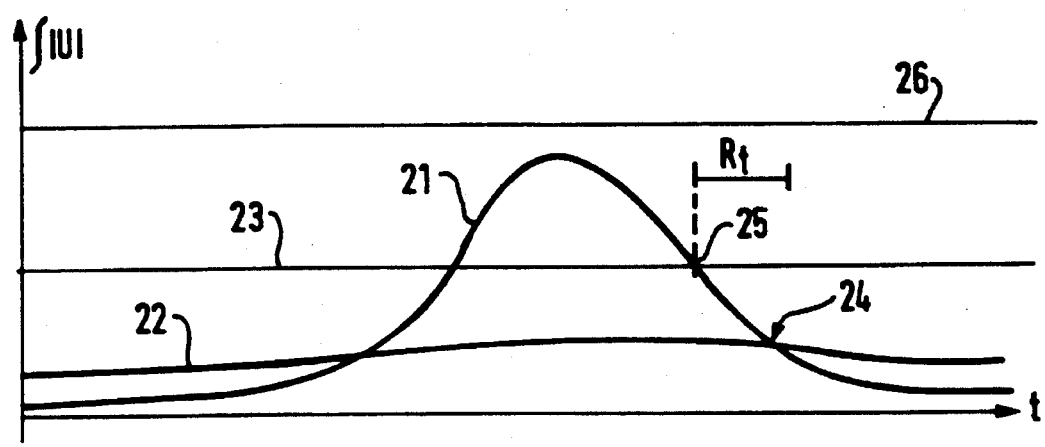
FIG. 4 is a diagram illustrating the functioning of the detector of FIG. 2.

In FIG. 4, the functioning of the detector 10 is illustrated by means of a diagram in which the output signal from the first integrator 14 is designated 21, and the output signal of the second integrator 15 is designated 22. The value of the briefly integrated signal 21 increases when an event occurs, causing it to exceed a detection level 23. This portion of the signal 21 is accepted as a detected spontaneous event because it does not exceed a threshold value 26, set higher than the detection level 23. The detection level 23 and the threshold level 26 are set on the basis of the signal 22 having the longer integration duration, which corresponds to the current (prevailing) level of noise. For example, the detection level can be set at half of the average value of peak values of the briefly integrated signal 21 in the last five events, plus a normalized lowest value for the signal 22 having a longer integration duration. The level of detection should not be permitted to drop below a defined value.

When the rising portion of the briefly integrated signal 21 passes the detection level 23, a refractory period is started, during which the microprocessor 16 renders detector 10 unable to approve additional events. When the decreasing side of the briefly integrated signal 21 again passes the detection level 23, at the location designated 25 in FIG. 4, a clock starts in the microprocessor 16 which sets the refractory period at a defined time $R_r$, for example, 25 ms.

Alternatively, the end of the refractory period can be set to occur when the decreasing side of the briefly integrated signal 21 passes the signal 22 having a longer integration duration, at the location designated 24 in FIG. 4.

In addition, a refractory period, whose expiration can be set in one of the ways described above, starts after an emitted stimulation pulse.

A second embodiment of the invention is shown in FIG. 5 wherein the detector 30 contains a signal conditioning unit 31 in which the electrical input signal is amplified, filtered and A/D-converted before being supplied to the remainder of the detector 30. The output signal from the signal conditioning unit 31 is then supplied over three parallel signal channels. In the first channel, the signal is rectified in a rectifier 32 and supplied to a first integrator 33 in which the rectified signal is integrated over a long integration interval in the same way as in the previously-described detector 10 in FIG. 2. In the second channel, the signal is supplied to a second integrator 35 which integrates the positive part of the signal over a brief integration interval. In the third channel, the signal is supplied to a third integrator 36 which integrates the negative part of the signal over a brief integration interval. The sum of the absolute values for the output signals from the second integrator 35 and the third integrator 36 is the same as the output signal from the briefly integrating integrator 14 shown in FIG. 2. All of the integrated signals are sent to a microprocessor 34, in which detection levels and threshold levels can be set in the same way as in the microprocessor 16 shown in FIG. 2. The microprocessor 34 in the embodiment of FIG. 5, however, can also distinguish between monophasic and biphasic signals. When the tissue in which events is being detected is that of a heart, this means that signals originating in the atrium can be distinguished from signals originating in the ventricle and signal originating in the ventricle can also be distinguished from signals originating in the atrium.

Although modifications and changes may be suggested by those skilled in the art, it is the intention of the inventors to embody within the patent warranted hereon all changes and modifications as reasonably and properly come within the scope of their contribution to the art.

We claim as our invention:

1. A detector for sensing events in living tissue comprising:

means for integrating the totality Of an incoming electrical signal from living tissue over a predetermined integration interval to obtain an integrated signal; and a microprocessor comprising comparator means for comparing said integrated signal with a signal detection level stored in said microprocessor and for generating an output signal indicating the occurrence of an event if said integrated signal exceeds said signal detection level.

2. A detector as claimed in claim 1 wherein said microprocessor comprises means for additionally comparing said integrated signal with a threshold level, stored in the microprocessor, higher than said detection level and for generating an output signal indicating the occurrence of an event if said integrated signal exceeds said signal detection level but does not exceed said threshold level during a comparison interval set by said microprocessor.

3. A detector as claimed in claim 2 wherein said microprocessor further comprises:

means for setting a number of events;

means for identifying a peak value of the integrated signal in each event;

averaging means for averaging the respective peak values of said number of events during a further comparison interval, set by said microprocessor which begins after said integrated signal has exceeded said signal detection level, to obtain an average value; and means, supplied with said average value, for setting at least one of said signal detection level and said threshold level dependent on said average value.

4. A detector as claimed in claim 3 wherein said microprocessor comprises means for setting said detection level at a first fraction of said average value and for setting said threshold value at said average value plus a second fraction of said average value.

5. A detector as claimed in claim 1 further comprising:

further integrator means for integrating the totality of said incoming electrical signal over a further integration interval which is longer than said integration interval of said integrator means and for generating a compensatory signal corresponding to prevailing noise superimposed on said incoming electrical signal; and wherein said microprocessor comprises means, supplied with said compensatory signal, for altering at least one of said integrated signal and said signal detection level dependent on said compensatory signal to compensate for prevailing noise.

6. A detector as claimed in claim 5 wherein said further integration interval of said further integration means is in a range of 5 to 20 times longer than said integration interval of said integrator means.

7. A detector as claimed in claim 1 wherein said microprocessor comprises means for additionally comparing said integrated signal with a threshold level higher than said signal detection level and for generating an output signal indicating the occurrence of an event if said integrated signal exceeds said signal detection level but does not exceed said threshold level during a comparison interval stored in said microprocessor, and said detector further comprising:

further integrator means for integrating the totality of said incoming electrical signal over a further integration interval which is longer than said integration interval of said integrator means and thereby generating a compensatory signal corresponding to prevailing noise superimposed on said incoming electrical signal; and wherein said microprocessor comprises means, supplied with said compensatory signal and with said average value, for altering at least one of said integrated signal, said detection level and said threshold level dependent on said average value and said compensatory signal.

8. A detector as claimed in claim 7 wherein said further integration interval of said further integration means is in a range of 5 to 20 times longer than said integration interval of said integrator means.

9. A detector as claimed in claim 1 further comprising rectifier means for rectifying said incoming electrical signals before said incoming electrical signals are integrated in said integrator means.

10. A detector as claimed in claim 1 wherein said incoming electrical signals comprises portions respectively having a first polarity and a second polarity, and wherein said integrator means further comprises first polarity integrator means for integrating the portions of said incoming electrical signals having said first polarity and second polarity integrator means for integrating the portions of said incoming signals having said second polarity.

11. A detector as claimed in claim 1 wherein said integrator means comprises means for emitting said integrated signal at intervals which are shorter than said integration interval.

12. A detector as claimed in claim 1 wherein said microprocessor comprises means for inhibiting sensing of events during a defined refractory period following each identified occurrence of an event.

13. A detector as claimed in claim 12 wherein said microprocessor comprises means for setting an end of said refractory period at a defined interval after said integrated signal falls below said detection level after an identified occurrence of an event.

14. A detector as claimed in claim 1 further comprising:

further integrator means for integrating the totality of said incoming electrical signal over a further integration interval which is longer than said integration interval of said integrator means and thereby generating a compensatory signal corresponding to prevailing noise superimposed on said incoming electrical signal;

wherein said microprocessor comprises means for inhibiting sensing of events during a defined refractory period following each identified occurrence of an event; and wherein said microprocessor comprises means for setting an end of said refractory period when said integrated signal falls below said compensatory signal.

* * * * *